(12) United States Patent
Jalali et al.

(10) Patent No.: US 9,784,661 B2
(45) Date of Patent: Oct. 10, 2017

(54) PARALLEL FLOW CYTOMETER USING RADIOFREQUENCY MULTIPLEXING

(71) Applicant: THE REGENTS OF THE UNIVERSITY OF CALIFORNIA, Oakland, CA (US)

(72) Inventors: Bahram Jalali, Los Angeles, CA (US); Eric Diebold, Los Angeles, CA (US); Brandon Buckley, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/263,419

(22) Filed: Sep. 13, 2016

(65) Prior Publication Data

US 2017/0227444 A1 Aug. 10, 2017

Related U.S. Application Data

(63) Continuation of application No. PCT/US2015/021264, filed on Mar. 18, 2015.
(Continued)

(51) Int. Cl.
*G01N 15/14* (2006.01)
*G01N 21/64* (2006.01)
*G01N 15/10* (2006.01)

(52) U.S. Cl.
CPC ......... *G01N 15/1434* (2013.01); *G01N 21/64* (2013.01); *G01N 21/6428* (2013.01);
(Continued)

(58) Field of Classification Search
CPC ........... G01N 21/6458; G01N 21/6486; G01N 21/6428; G02B 21/16
(Continued)

(56) References Cited

U.S. PATENT DOCUMENTS 6,592,822 B1 7/2003 Chandler
7,630,063 B2 12/2009 Padmanabhan et al.
(Continued)

FOREIGN PATENT DOCUMENTS

WO 2014/152048 A2 9/2014

OTHER PUBLICATIONS

Korean Intellectual Property Office (KIPO), International Search Report and Written Opinion, PCT International Application No. PCT/US2015/021264, issued Jun. 5, 2015, pp. 1-11, with claims searched, pp. 12-18.
(Continued)

*Primary Examiner* — David Porta
*Assistant Examiner* — Meenakshi Sahu
(74) *Attorney, Agent, or Firm* — Bret E. Field; Bozicevic, Field & Francis LLP

(57) ABSTRACT

An imaging flow cytometry apparatus and method which allows registering multiple locations across a cell, and/or across multiple flow channels, in parallel using radio-frequency-tagged emission (FIRE) coupled with a parallel optical detection scheme toward increasing analysis throughput. An optical source is modulated by multiple RF frequencies to produce an optical interrogation beam having a spatially distributed beat frequency. This beam is directed to one or more focused streams of cells whose responsive fluorescence, in different frequencies, is registered in parallel by an optical detector.

31 Claims, 7 Drawing Sheets

Related U.S. Application Data

(60) Provisional application No. 61/955,137, filed on Mar. 18, 2014.

(52) U.S. Cl.
CPC ..... *G01N 21/6458* (2013.01); *G01N 21/6486* (2013.01); *G01N 2015/1006* (2013.01); *G01N 2021/6421* (2013.01); *G01N 2201/067* (2013.01)

(58) Field of Classification Search
USPC ...................................................... 250/459.1
See application file for complete search history.

(56) References Cited

U.S. PATENT DOCUMENTS 9,423,353 B2 *   8/2016   Diebold ............. G01N 21/6458
2012/0307244 A1  12/2012  Sharpe et al.

OTHER PUBLICATIONS

Diebold et al., "Digitally synthesized beat frequency multiplexing for sub-millisecond fluorescence microscopy", Nature Photonics, Oct. 2013, vol. 7, No. 10, pp. 806-810, published online Sep. 22, 2013.
Eisenstein, Michael, "Fluorescence microscopy gets a frequency boost", Nature Methods, Dec. 2013, vol. 10, No. 12, p. 1149.

* cited by examiner

FIRE linescan
in flow, $\tau_{exp}$ = 1.25 μs
v = 1 m/s 28  39  50  61  72
frequency (MHz)

Widefield (EMCCD)
in flow, $\tau_{exp}$ = 10 μs
v = 1 m/s

Widefield (CMOS)
stationary, $\tau_{exp}$ = 200 ms
v = 0 m/s ize_patent

PARALLEL FLOW CYTOMETER USING RADIOFREQUENCY MULTIPLEXING

CROSS-REFERENCE TO RELATED APPLICATIONS

This application is a 35 U.S.C. §111(a) continuation of PCT international application number PCT/US2015/021264 filed on Mar. 18, 2015, incorporated herein by reference in its entirety, which claims priority to, and the benefit of, U.S. provisional patent application Ser. No. 61/955,137 filed Mar. 18, 2014, incorporated herein by reference in its entirety. Priority is claimed to each of the foregoing applications.

The above-referenced PCT international application was published as PCT International Publication No. WO 2015/143041 on Sep. 24, 2015, which publication is incorporated herein by reference in its entirety.

STATEMENT REGARDING FEDERALLY SPONSORED RESEARCH OR DEVELOPMENT

This invention was made with Government support under Grant Number W81XWH-10-1-0518, awarded by the U.S. Army, Medical Research and Materiel Command. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technological Field

This technical disclosure pertains generally to flow cytometry, and more particularly to a parallel flow channel flow cytometer utilizing optical beams uniquely modulated for each flow channel.

2. Background Discussion

Flow cytometry is a biotechnology utilized to analyze the physical and chemical characteristics of particles in a fluid. Flow cytometry is utilized in cell counting, cell sorting, biomarker detection and other microbiological and medical processes. Cells are suspended in a stream of fluid in a channel(s) which pass by an optical detection apparatus. Various physical and chemical characteristics of the cells are analyzed (multiparametric analysis).

Applications for flow cytometry include diagnostics, clinical, and research, including immunology, virology, hematology, and drug discovery, and so forth. It will be noted that drug discovery is an extremely expensive and lengthy process, in which high speed cytometry plays a key role. Development costs are in the billions of dollars, spanning over more than a decade. Average costs have been seen over $5 billion to develop each drug, which is partially due to the fact that for every drug developed successfully, several fail. Perhaps even more problematic is that even with steadily increasing discovery and development costs, the efficiency of finding new drugs is decreasing. It has been reported that the number of drugs discovered per billion dollars spent is halving approximately every 9 years. A strong incentive thus exists to improve all aspects of the drug discovery process and elsewhere.

Within the overall drug discovery pipeline, the most common technique for discovering lead compounds that eventually become drugs is high throughput screening (HTS). In HTS, hundreds of thousands (or even millions) of compounds are assayed against a disease target. Today, this costly and lengthy process is often performed in large-scale laboratories, often involving automated robotics and instrumentation, alongside high performance computing. Within the HTS field, it is widely acknowledged that there is a general and pressing need for inexpensive compound screening assays and tools that quickly yield accurate, high content data in order to reduce the cost of drug discovery and the time-to-market of novel therapeutic agents. Any technique that can provide even a moderate advance in this area has an enormous potential to dramatically reduce costs and improve the overall efficiency.

Flow cytometry is also an established research tool used in many areas of cell biology that provides high content single-cell data by using a combination of optical scattering and multi-color fluorescence measurements. While not yet widely used in high throughput compound screening, the multi-parameter, phenotypic information yielded by flow cytometry offers significant advantages over the conventional approach of using several separate single-parameter, population-averaged measurements to determine the effect of a candidate compound on a target. By measuring many parameters simultaneously from populations of single cells using flow cytometry, complex intra- and inter-cellular interactions within a cell or cellular population can be more quickly elucidated than with well-level screens (e.g., luminescence, absorbance, ELISA, NMR, time resolved fluorescence, FRET, and the like). This high content, multiparameter data inherently yields deeper insight into the effect a compound may ultimately have on a patient during clinical trials, and may potentially reduce or eliminate the need for further downstream assays in the drug discovery pipeline (e.g., by performing a receptor binding or gene reporter assay concurrently with a cell viability/apoptosis assay).

Despite the undoubted benefits of flow cytometry in drug discovery and other applications, the throughput of modern flow cytometry (e.g., on the order of 10,000 cells per second) is insufficient to perform screening of the large compound libraries available today at pharmaceutical and biotechnology companies. For high throughput screening to yield a reasonable number of hits in a short period of time, hundreds of thousands of compounds must be screened each day. Further, the sheer cost of developing and performing screening assays demands that they are completed in a reasonable amount of time, given the already long and expensive further testing and clinical trials that await such candidate drugs.

Efforts have been made to improve the speed of cytometry and sample handling, such as development of the Hyper-Cyt® autosampler from Intellicyt Corporation®. These efforts have enabled the use of flow cytometry at improved speeds, enabling a 384-well plate to be screened using 1-microliter samples in approximately 20 minutes. This advance has opened the door for using flow cytometry in drug screening, yet the technique is still at least an order of magnitude slower than fluorescence plate or microarray readers.

While the HyperCyt autosampler has vastly improved the ability of flow cytometry to perform compound screening, the instrument serially multiplexes samples from plate wells into a single stream. It can interrogate only one well at a time, which limits the throughput (in wells/hour) of the entire screening system. Conventional flow cytometers offer sufficient throughput (10,000 cells/second) to interrogate all of the cells in the microliter volumes sampled by the HyperCyt during each well period, and as such, the autosampler is the bottleneck to the speed of the screen. At 20 minutes per 384 well plate, this system is capable of examining approximately 25,000 wells per day. While this represents a substantial throughput, it is four times slower than the industry standard HTS goal of 100,000 wells (or more) per day. While there are ongoing efforts to improve on this number by running several flow cytometers in parallel from multi-probe autosamplers, the cost of these multi-instrument systems quickly becomes prohibitively large. Additionally, the complexity of calibrating and controlling multiple independent instruments can yield unreliable data, making interpretation of assay data difficult.

Regardless of these difficulties, the Genomics Institute of the Novartis Research Foundation (GNF) has recently built a multimillion dollar high-throughput flow cytometry screening system, which at its core, consists of a three-probe autosampler attached to three independent Beckman-Coulter CyAn flow cytometers. Due to the rich assay data it provides, GNF personnel have reportedly used this system intensely. This example clearly demonstrates the utility of flow cytometry in drug discovery, and the need to improve the cost and simplicity of these systems.

Accordingly, a need exists for a parallel flow cytometry apparatus and method that can significantly increase throughput. The present disclosure provides this increased throughput while overcoming shortcomings of previous approaches.

BRIEF SUMMARY

The disclosed parallel flow cytometry overcomes numerous limitations found in current instrumentation by employing simultaneous probing of parallel flow channels in a new manner. By way of example, and not of limitation, the disclosure combines photomultiplier tube (PMT) based fluorescence analysis using radio-frequency-tagged emission (FIRE) optical detection scheme with a microfluidic device.

An optical engine is disclosed for a highly-parallel flow cytometer which improves sample screening throughput by an order of magnitude, such as 200 wells per minute. In at least one embodiment, the disclosed apparatus and method can be integrated with a commercial multi-probe autosampler.

The disclosed technology drastically reduces both the time and cost requirements of high throughput compound screens using flow cytometry. Inherently, the ability to use multi-parameter flow cytometry provides richer information than instruments, such as plate readers, due to the high content cell-level information provided, and the ability to measure sub-populations within the sample wells. While high content imaging also provides many of these advantages, it is not very effective when utilized with suspension cells, and requires sophisticated image processing and data handling to extract meaningful parameters from samples.

Further aspects of the presented technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The disclosed technology will be more fully understood by reference to the following drawings which are for illustrative purposes only:

DETAILED DESCRIPTION

Figure 1A:
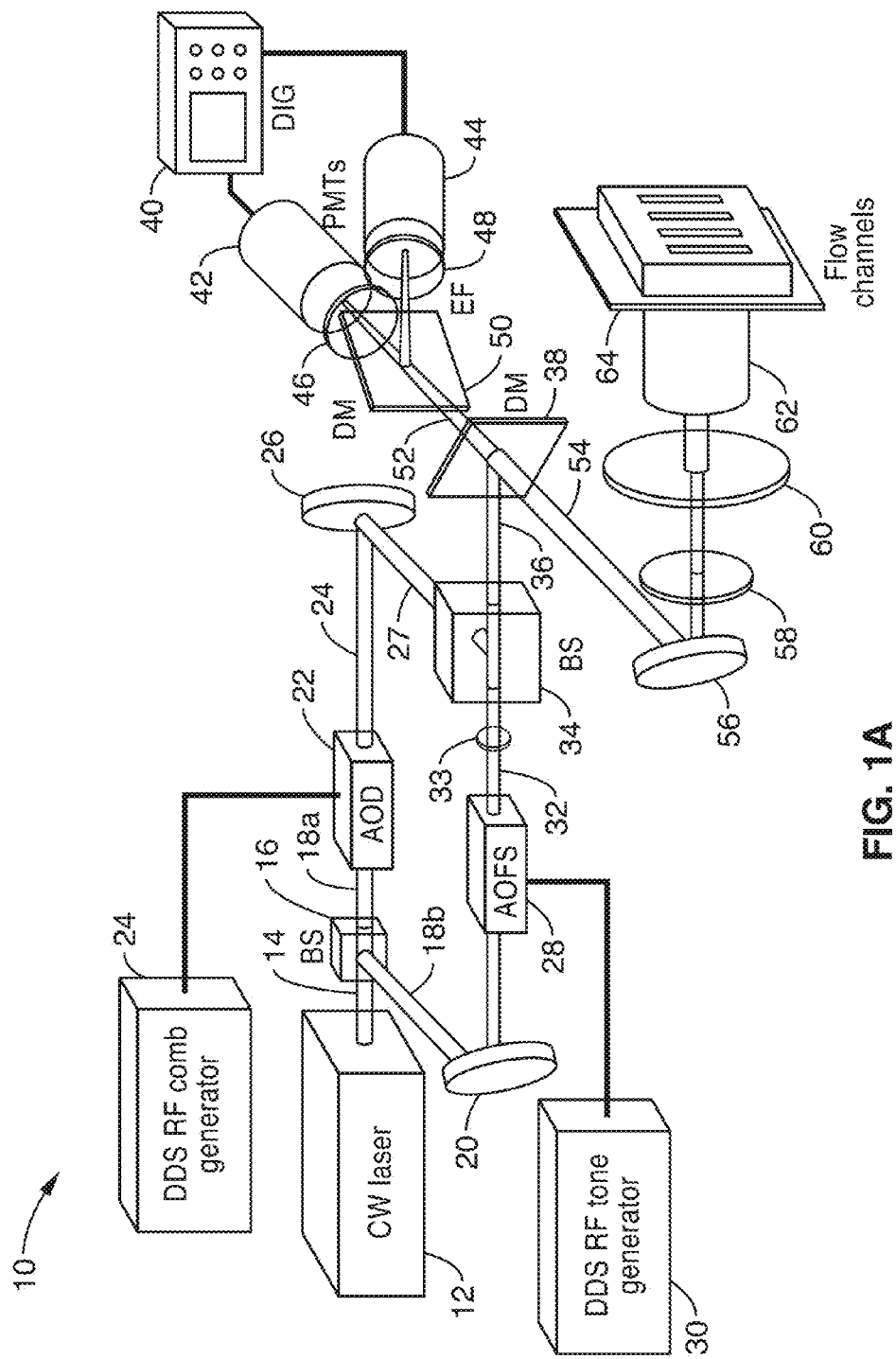
FIG. 1A through FIG. 1D are block diagrams of parallel flow cytometry using radio frequency tagging of parallel channels using a single optical system according to an embodiment of the present disclosure.

1. Innovation.

The present disclosure provides a single cytometer that is capable of sampling and reading a plurality of wells (e.g., 10) in parallel, for enhancing flow cytometry throughput, such as utilized in applications like drug discovery. Although many commercial options for parallel liquid sample sipping/aspiration and handling, there have been no existing instruments that could interrogate multiple cells in parallel at high speed with sufficient optical sensitivity. While several microfluidic approaches to parallel flow cytometry have been demonstrated, these systems employed laser scanning illumination, or silicon high-speed cameras as optical detectors. These demonstrations had two primary limitations: (1) laser scanning does not support parallel analysis of cells flowing at meter/s velocities due to the limited duty cycle of the laser exposure on each channel; (2) silicon cameras although useful for imaging brightly-illuminated scenes at high speed, neither possess (i) sufficient shutter speed to avoid image blur, (ii) sufficient readout speed for the high event rates in flow cytometry, nor (iii) the required shot-noise limited optical sensitivity to accurately detect the small number of fluorescence photons emitted by cells during their microsecond transit times through the optical interrogation regions. The system of the present disclosure does not suffer from these shortcomings.

A flow cytometry system of one embodiment, is configured for interrogating a plurality (e.g., from two to ten or more) independent focused streams of cells with multi-color fluorescence (FITC, PE), and forward and side-scatter detection. In this embodiment, a FIRE optical engine is preferably utilized in combination with an inertially focused microfluidic chip. It should be appreciated, however, that the present disclosure may be implemented with cells that are focused using hydrodynamic focusing, sheath flow focusing, acoustic focusing, other types of particle focusing methods, and combinations thereof. In addition, it should be appreciated that although described as being utilized with cells, the device of the present disclosure can be utilized for analyzing streams of various particles, including cells, beads, pieces of cells, and so forth.

Another embodiment accomplishes the forgoing by further including frequency tagging of the excitation/emission light incident on the plurality of separate flow microchannels allowing detection and analysis in a low-cost single optical system. This obviates the need for many parallel optical trains, filters, and expensive detectors. As a consequence of every flow channel being illuminated at a different modulation frequency, a single PMT detector can be utilized to detect light (of a single color, as a fluorescence filter is used) from multiple points, when the resulting electrical signal is analyzed using signal processing. Signals from particles in each flow channel are thus encoded in the frequency domain.

By utilizing the disclosed technology, each stream in the system becomes capable of measurement throughput comparable to modern flow cytometers, (e.g., greater than 10,000 events/second), while the overall system will be capable of simultaneously handling a plurality, in this example 10, independent samples, thereby speeding up HTS using flow cytometry by an order of magnitude. Using a different microfluidic chip, the disclosed technology will also be adaptable to handle single samples at rates exceeding 100,000 events/second for other applications, such as rare cell detection (circulating tumor cells, cancer stem cells, circulating endothelial cells, and so forth.), or simply to speed up data acquisition from large samples.

The benefits of the combination of these innovations in such a system can be summarized as follows: (a) FIRE is configured on the system to independently-control the illumination of each parallel flow stream, which is critical to the system calibration in order to establish each flow channel with identical optical sensitivity. (b) FIRE is configured on the system to utilize a single PMT for each fluorescence or scatter measurement, avoiding the use of slow and insensitive cameras. This means the number of PMT's does not scale linearly with the sample throughput of the system, but rather with the number of parameters measured. Each PMT has a fluorescence emission filter in front of it, such that it detects one color of fluorescence emission from all flow channels at the same time. The operational principles of the technology are described in greater detail below.

A. Fluorescence Imaging Using Radiofrequency-Tagged Emission (FIRE)

FIRE is an ultra-high speed fluorescence imaging technique developed at UCLA to meet the speed demands of high throughput fluorescence imaging flow cytometry and sub-millisecond fluorescence microscopy. The central feature of FIRE microscopy is its ability to excite fluorescence in each individual point of the sample at a distinct radiofrequency, which allows detection of fluorescence from multiple points using a single photodetector. This excitation occurs at the beat frequency between two interfering, frequency-shifted beams of light.

FIG. 1A through FIG. 1D illustrate one embodiment 10 of utilizing

FIRE for parallel flow cytometry using radiofrequency multiplexing according to the present disclosure. A laser 12 (e.g., 488-nm excitation) outputs beam 14, which is split by beamsplitter 16 (e.g., non-polarizing) into two beams 18a, 18b in the arms of a Mach-Zehnder interferometer. The light in the first arm 18a is frequency shifted by an acousto-optic deflector (AOD) 22, which is driven by a phase-engineered radiofrequency comb 24, designed to minimize signal peak-to-average power ratio. As seen in FIG. 1B, this RF comb causes AOD 22 to generate multiple deflected optical beams 24 possessing a range of both output angles as well as frequency shifts. Output from AOD 24 is returned back for combination with the other arm by mirror 26. It should be appreciated that interoperation between the excitation beam with a plurality of fluid channels requires the RF comb generator to be configured to generate a spatially disparate amplitude modulated beam. If configured for collecting images, the frequencies in the comb are too closely spaced for analyzing separate flow streams. This configuration of the RF comb generator could be referred to as a 'sparse' frequency mode.

The second arm of the interferometer has beam 18b reflected from mirror 20 to then be shifted in frequency using an acousto-optic frequency shifter (AOFS) 28 receiving a signal from a direct digital synthesis (DDS) radiofrequency (RF) tone generator 30 to generate a local oscillator (LO) beam 32.

A cylindrical lens 33 placed after the AOFS matches the angular divergence of the LO arm to that of the RF comb beams. After combining beams 27 and 32 at a second beamsplitter 34, the two beams are focused 36 coincident to a line on the sample using a conventional laser scanning microscope lens system. Other configurations of one or more acousto-optic devices to generate frequency-shifted coincident pairs of beams are also disclosed. Alternatively, other system configurations, such as multiple electro-optic, liquid crystal, or other light modulators can be employed to amplitude modulate multiple independent excitation optical beams at more than one unique frequency, such that a single PMT detector can be used to analyze the fluorescence or scatter emission from all flow channels simultaneously.

The microscope lens system is shown with a dichroic mirror (DM) 38 that provides different reflective/transmissive properties at two different wavelengths. Dichroic mirror 38 reflects the pump laser light, and transmits longer wavelength light, while dichroic mirror 50 splits the different colors of fluorescence emission so that each PMT can analyze the amount of light in the different spectral bands. It will be appreciated that dichroic mirror 50 operates in combination with filters 46, 48, as a means for separating different colors of fluorescence emission. The present invention is not limited to using a mirror-filter combination for separating bands of fluorescence emission, as a number of techniques are known for performing optical separation with respect to frequency band. Beam 54 from DM 38 is reflected from mirror 56 through a lens system 58, 60 to an objective 62, in which the flow channels 64 are coupled for being read. It should be recognized that the optics in the illustrated configuration are not configured with angular scanning mechanisms, such as using a scanning mirror for mirror 56, as might be utilized when capturing images. In the present disclosure, data is collected on a discrete point (or a few points) across the width of a sample from which analysis is performed.

An optical signal returned back from objective 62 passes through the lenses 58, 60, mirror 56 and through DM 38 as beam 52, strikes the second DM 50 and separates into beams that pass through fluorescence emission filters (EF) 46, 48, to photomultiplier tubes 42, 44, which are being read by a digitizing storage system 40, such as an analog to digital converter, a digitizing oscilloscope, a multi-channel lock-in amplifier, or another high speed data acquisition system.

It should be appreciated that the photomultiplier tubes are not imaging devices in their conventional use, but operate to multiply photon activity from a source beam, and convert it to an electrical output. Each PMT is utilized for collecting information about a specific characteristic of the particles being analyzed, because these different characteristics have been tagged with fluorophores operating at different wavelengths. It is recognized that fluorophores absorb light energy of a specific wavelength (range) and re-emit light at a longer wavelength.

Figure 1B:
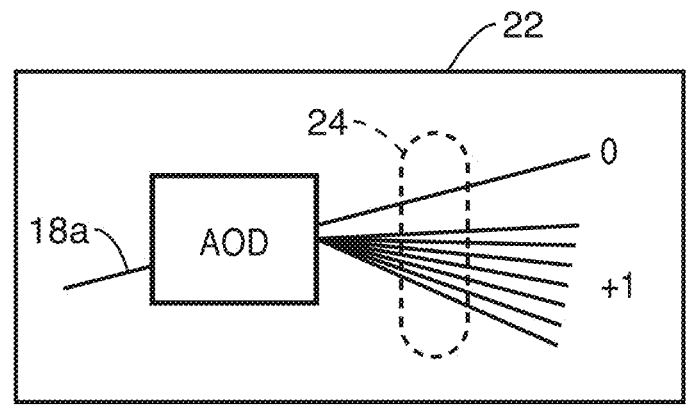
Figure 1C:
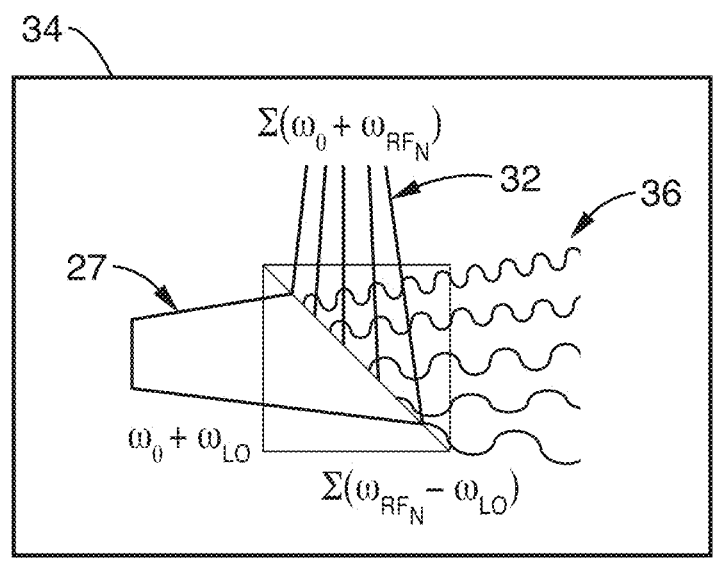

In FIG. 1C, the optical wave interaction at beamsplitter 34 is depicted with a first signal 27 ($\omega_0+\omega_{LO}$) interacting with second signal 32 $\Sigma(\,(\omega_0+\omega_{RF_N})$ to output a combined signal 36 $\Sigma(\,(\omega_{RF_N}-\omega_{LO})$. These output beams represent the range of frequencies contained in the amplitude modulated beams that excite particles in the parallel flow channels 70, shown in FIG. 1D.

Since fluorescent molecules in the sample function as square-law detectors (their excitation responds to the square of the total electric field), the resulting fluorescence is emitted at the various beats defined by the different frequencies of the two arms of the interferometer. Further, since acousto-optic devices are inherently resonant devices, the acousto-optic frequency shifter (AOFS) 28 in the second arm of the interferometer is chosen to heterodyne the beat frequencies to baseband, in order to maximize the useable bandwidth for a given fluorophore. In this case, an AOFS is utilized, but other implementations utilize a second AOD or other acousto-optic device, and can be driven by a single electronic tone, or a frequency comb.

For the sake of simplicity of illustration, FIG. 1A depicts only two PMTs being used, however, more PMTs can be added for simultaneously registering additional particle characteristics across the plurality of flow channels. In one embodiment, cylindrical lens 33 placed after the AOFS to match the divergence of the LO beam to that of the RF beams, is replaced by using two AODs (at the position of the AOFS, but with no cylindrical lens used) of opposite diffraction orders are used to generate discrete interrogation beams at the sample.

Figure 1D:
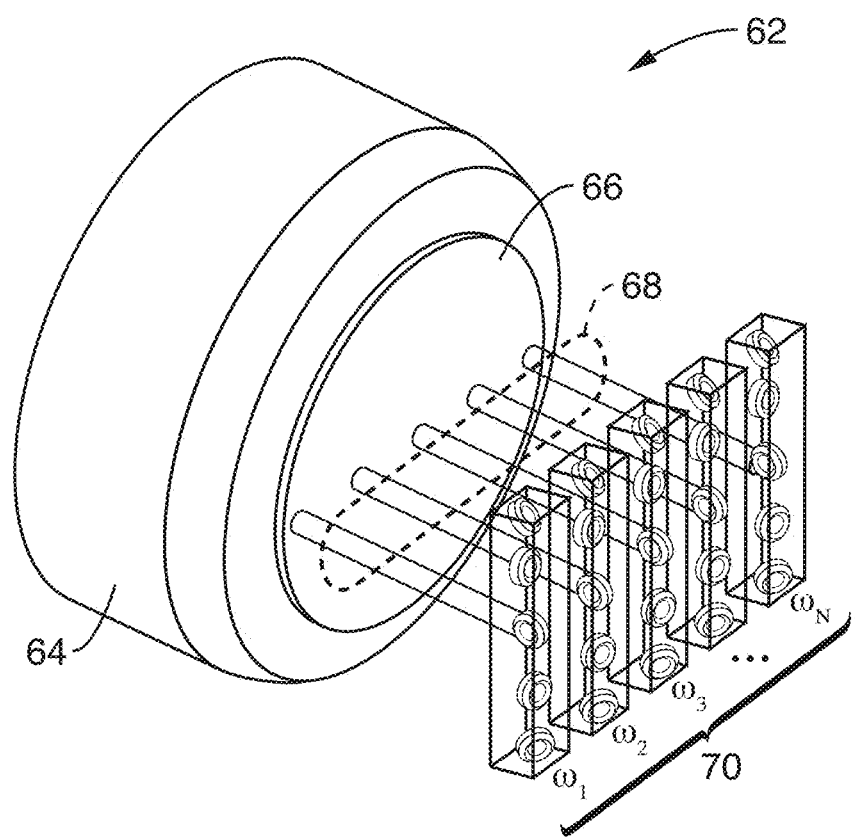

FIG. 1D is a close-up view of an example embodiment 62 of the multi-channel interrogation approach of the present disclosure. Cells in multiple flow channels 70 ($w_1$, $w_2$, $w_3$, ... $w_N$) are excited in parallel by beams 68 modulated at unique beat frequencies, passing through objective 64 and lens 66. In at least one embodiment (not shown), forward scatter PMT detector is included in the final cytometer design. Backscatter detection can replace the conventional side-scatter detection channel, by using a PMT in a similar position to PMTs 42 and 44.

FIRE operates by simultaneously exciting fluorescence from distinct points on the sample at a unique radiofrequency. Since the excitation (and hence, emission) from each point is tagged with a unique frequency, a single PMT can be used to collect epi-fluorescence from multiple spatial points, and a Fourier transform of the output signal is used to analyze the fluorescence emission of the sample, for example, of an array of parallel flow channels. To excite fluorescence at pre-defined locations in multiple individual streams of cells, the optical design is configured such that a plurality of discrete points (e.g., 10 discrete points) is illuminated by amplitude modulated beams or pairs of frequency-shifted beams. Illumination at the plurality of discrete points is a configuration to maximize the amount of laser power incident upon each flow channel, without wasting laser power on the regions between the flow channels, as would be the case when using an AOFS and cylindrical lens, although this embodiment of the system still enables analysis of multiple flow channels using single element detectors.

Figure 2A:
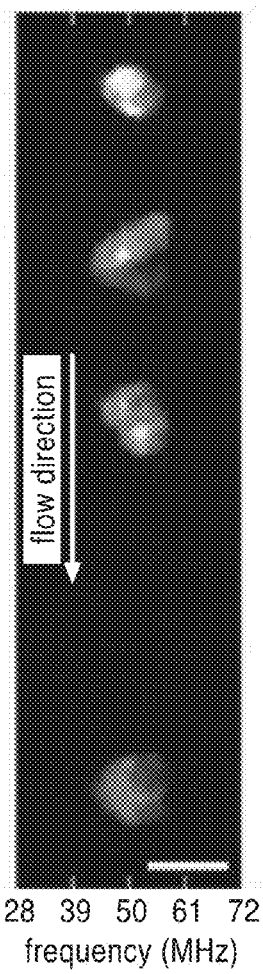
FIG. 2A through FIG. 2G are images captured using high-speed imaging flow cytometry according to an embodiment of the present disclosure.
Figure 2B:
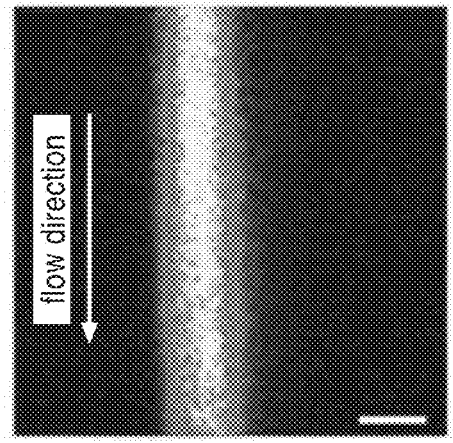
Figure 2C:
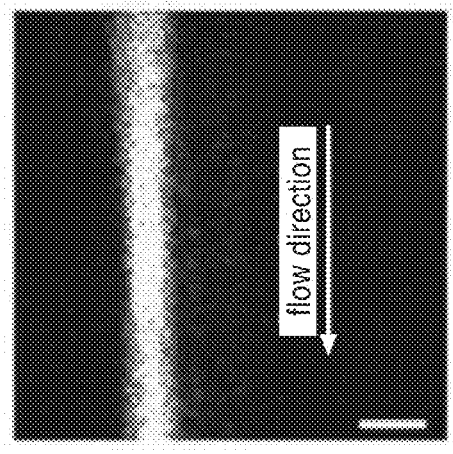
Figure 2D:
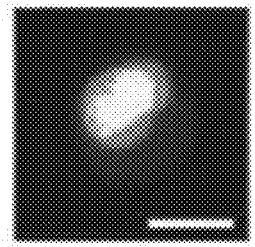
Figure 2E:
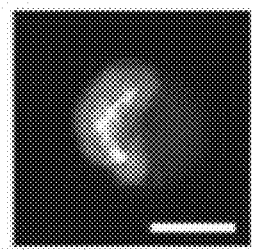
Figure 2F:
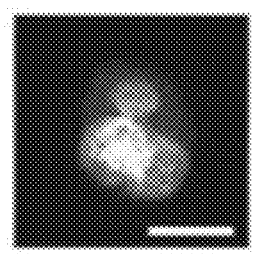
Figure 2G:
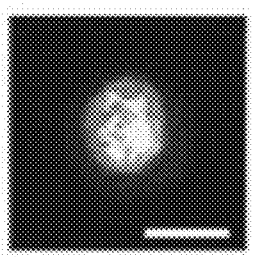

FIG. 2A through FIG. 2G depict results from experiments using FIRE to perform imaging flow cytometry to show what fluorescence imaging can depict from a single particle in a stream. In this example, MCF-7 breast carcinoma cells are shown flowing in a microfluidic channel at a velocity of 1 m/s. All images are of MCF-7 breast carcinoma cells, stained with the DNA stain Syto16, taken using a 60×, 0.70-NA objective lens. In FIG. 2A is seen representative FIRE images of cells flowing at a velocity of 1 m/s, taken using a pixel frequency spacing of 800 kHz, and 54 μW of 488-nm laser power per pixel, measured before the objective. FIG. 2B and FIG. 2C depict single 10-ps exposure frame transfer EMCCD images of individual cells flowing at a velocity of 1 m/s for comparison. The electron multiplier gain was adjusted to produce maximal image SNR, and the EMCCD vertical shift time was set to the minimum value of 564 ns. Blur is observed in the image due to the long exposure time and the frame transfer nature of the EMCCD. In FIG. 2D through FIG. 2G wide field fluorescence images are represented of stationary MCF-7 cells for morphological reference. All scale bars are 10 μm. However, it should be appreciated that the present disclosure is not configured for performing imaging on cells in a single stream, but instead to simultaneously analyzing at least one discrete point in each of a plurality of flow streams. Examples of the types of information provided by the presented technology are described in FIG. 3 through FIG. 4B.

These preceding tests serve to illustrate the ability of the FIRE technology to use a single PMT detector to simultaneously interrogate cellular fluorescence with high sensitivity (54 μW of laser excitation power is used per pixel) from 125 distinct spatial pixels at high speed. By reducing the number of pixels from 125 to 10 (using one ~50 μm×10 μm "pixel" per flow stream) the optical sensitivity of the system improves dramatically (more than 10 dB). This is due to the fact that (i) the number of pixels multiplexed into the same PMT is reduced and (ii) shot noise crosstalk that results in multiple pixels being "on" at the same time is dramatically reduced, as the cell arrival times at the optical interrogation region on the microfluidic chip follows Poisson statistics, as opposed to the case of imaging, in which multiple adjacent pixels in an image are typically "on" simultaneously. However, if multiple cells are interrogated at the same time, digital post-processing can perform compensation of the fluorescence intensities to account for this shot noise crosstalk. The concept of compensation is ubiquitous in flow cytometry, and is typically used to account for the broad emission spectra of fluorophores. Shot noise compensation is actually simpler than spectral compensation, in that the compensation values are simply proportional to the square root of the average output current of the detector.

2. Methods and Materials

Design and Implementation of Parallel Optical Cytometry Engine and Parallel Microfluidic Chip.

The field of view, cell flow velocities, inertial focusing spatial distribution, and excitation laser spot sizes are designed for producing a combination of maximum throughput as well as maximum signal-to-noise ratio (SNR). The design goal is to record 10,000 events/second in each of a plurality of parallel channels (e.g., 10), all within a 1 mm field of view. By way of example and not limitation, a 488 nm laser is utilized for excitation, and existing digitizing electronics (e.g., 16-bit with memory depth capable of continuously storing data from more than 10"9 cells) are utilized to collect the data. Higher bit-depth commercially-available digitizers can be used for better intensity resolution, as desired. As the optical excitation and collection efficiency will vary from channel to channel, variations in the signals are measured using fluorescent reference beads.

To eliminate this variation, the laser power directed to each channel is adjusted, such as in software, by adjusting the MATLAB-generated waveform used to drive the acousto-optics. A 0.8-NA (or higher numerical aperture), 20× microscope objective is utilized to improve the detection sensitivity of the system (as compared to 0.45-NA, 20×). This parameter can be measured with the system of the present disclosure using standard techniques, and laser power can be increased to achieve this goal if not possible with a 100 mW 488 nm laser. More powerful lasers (e.g., greater than 1 W) exist that would further improve the sensitivity (dividing the power into 10 spots reduces the power per channel to approximately 50 mW per channel).

A. FIRE with Parallel Flow Channels.

From previous testing templates have been evaluated for fabricating massively parallel microfluidic chips. The present disclosure can be utilized separately with these chips, which have walls in between each stream. A variety of microfluidic chip designs can be envisioned that will work with the frequency multiplexed nature of the FIRE parallel flow cytometer. It should also be appreciated that hydrodynamic focusing, inertial focusing, or other techniques and combinations thereof can be utilized in the flow channels to align the cells in a variety of positions for interrogation using modulated optical beams.

Figure 3:
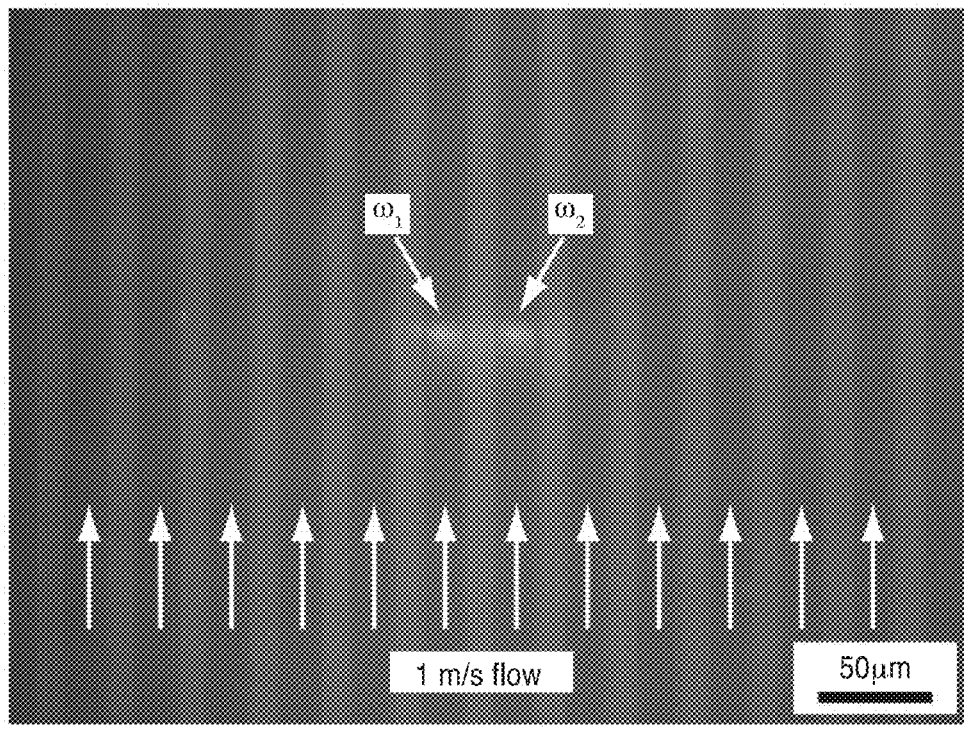
FIG. 3 is an image of parallel flow cytometry such as performed according to embodiments of the present disclosure.

FIG. 3 depicts a parallel flow through microfluidic channels, in which particles in those channels are all simultaneously detected/captured according to the presented technology. In the figure one sees a plurality of parallel flow channels, each marked with the vertical flow arrow. By way of example the image was captured with only two particles in the channels. In this demonstration, excitation and fluorescent response capture was performed using a similar setup to that of the disclosed technology. To demonstrate the ability of FIRE to perform flow cytometry measurements on distinct flow channels, single-point flow cytometry measurements were performed on fluorescent beads. The FIRE setup shown in the figure excites two parallel microfluidic channels on a chip fabricated using polydimethylsiloxane (PDMS) molding. A single sample, consisting of 1.0 µm ($\lambda_{ex}/\lambda_{em}$ 515/585 nm) and 2.2 µm ($\lambda_{ex}/\lambda_{em}$ 490/520 nm) fluorescent beads, was flowed through parallel channels at a mean velocity of 1 m/s using a syringe pump. Channels 1 and 2 were excited using a 488 nm laser, modulated at beat frequencies of 10 and 50 MHz, respectively.

Figure 4A:
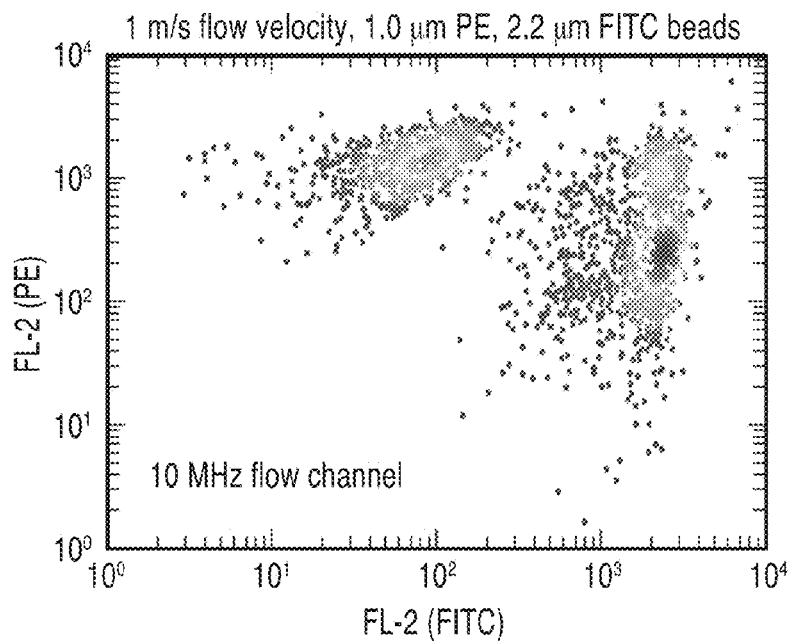
FIG. 4A and FIG. 4B are scatter plots of data collected at one or more discrete sites on a particle such as performed according to embodiments of the present disclosure.
Figure 4B:
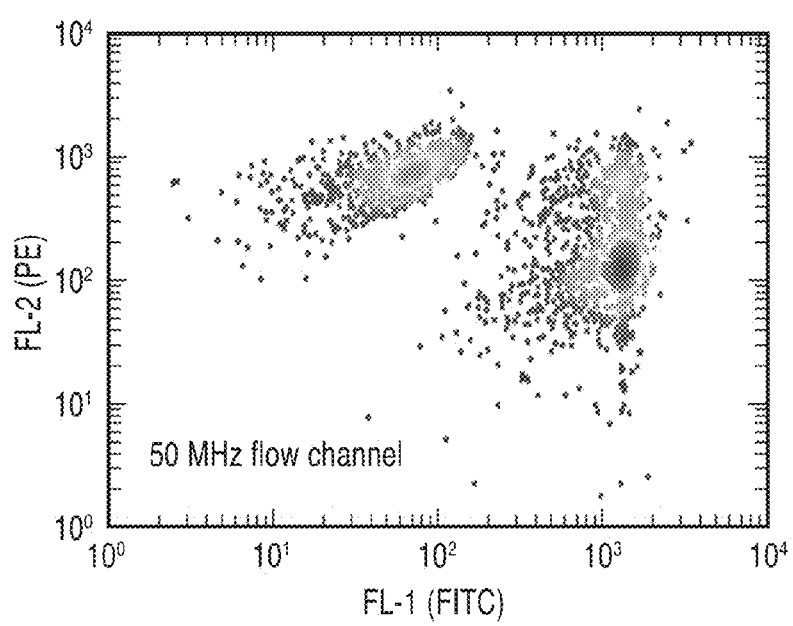

FIG. 4A and FIG. 4B depict scatter plots for the 10 MHz and 50 MHz flow channels after raw data was thresholded and the fluorescence pulses were integrated to create PE (red) vs. FITC (green) fluorescence intensity scatter plot. It will be noted that these plots are shown as monochromatic to simplify reproduction of the patent application. The two bead populations in both channels are clearly resolved, despite the low (8-bit) resolution of the digitizer used to collect the data (no log amplification was used). This experiment was run at a total throughput of approximately 70,000 beads/second (35,000 beads/second/flow channel). This preliminary result clearly shows the ability of FIRE to perform 2-color parallel conventional flow cytometry using a single photomultiplier tube detector to detect each fluorescence color simultaneously from multiple flow channels.

From the description herein, it will be appreciated that the present disclosure encompasses multiple embodiments which include, but are not limited to, the following:

1. An apparatus for simultaneously analyzing physical and chemical characteristics of particles in multiple streams of particles, the apparatus comprising: (a) at least one optical excitation source; (b) a first radio-frequency source having a first radio-frequency output; (c) a second radio-frequency source having a second radio-frequency output; (d) an optical, or acousto-optical, combining device configured for combining said first radio-frequency output and said second radio-frequency output into an optical interrogation beam having a spatially distributed beat frequency, wherein said optical interrogation beam comprises a plurality of separate beams configured for being directed to each of a plurality of focused streams; (e) an optical system configured for directing said optical interrogation beam across the plurality of focused streams of particles so that said spatially distributed beat frequency simultaneously spans said plurality of focused streams of particles whose physical and chemical characteristics are being analyzed by said apparatus; and (f) an optical detector configured for registering fluorescence of particles, within said plurality of focused streams of particles, at different modulation frequencies within said spatially distributed beat frequency, wherein fluorescence across multiple focused streams of particles are registered in parallel by said optical detector.

2. The apparatus of any preceding embodiment, wherein said optical excitation source comprises a laser.

3. The apparatus of any preceding embodiment, wherein said laser comprises a continuous wave laser.

4. The apparatus of any preceding embodiment, wherein said optical combining device, said optical system, or a combination thereof, are configured for independently-controlling illumination directed at each parallel flow stream, toward establishing each flow channel with identical optical sensitivity.

5. The apparatus of any preceding embodiment, wherein said plurality of focused streams of particles are retained in a microfluidic device or chip.

6. The apparatus of any preceding embodiment, further comprising one or more additional optical detectors, each of which are configured for registering fluorescence at a different modulation frequency so that different characteristics of particles in each focused stream are detected.

7. The apparatus of any preceding embodiment, further comprising optical means for separating different colors of fluorescence emission so that each of these multiple detectors can analyze fluorescence in a different spectral band associated with different characteristics of particles in each focused stream of particles.

8. The apparatus of any preceding embodiment, wherein each channel of a microfluidic device or chip is exposed to excitation at a different modulation frequency that is unique to that channel by using beat frequency modulation.

9. The apparatus of any preceding embodiment, wherein fluorescence is excited in each channel at a distinct radio-frequency, which allows detection of fluorescence from multiple points using a single photodetector.

10. The apparatus of any preceding embodiment, wherein said particles comprise cells, or portions of cells.

11. The apparatus of any preceding embodiment, wherein said optical, or acousto-optical, combining device comprises an interferometer, with the beam being split with a first arm of the beam received at an first acousto-optic device, and a second arm of the beam received by a second acousto-optic device, after which the arms of the beam are recombined and directed through the optical system.

12. The apparatus of any preceding embodiment, wherein said first or second acousto-optic device comprises an acousto-optic deflector (AOD), or an acousto-optic frequency shifter (AOFS).

13. The apparatus of any preceding embodiment, further comprising a radio frequency (RF) comb generator configured for driving said acousto-optic deflector thus generating a set of spatially disparate amplitude modulated beams through beat frequency modulation with sufficient spatial width to span said plurality of focused streams of particles.

14. The apparatus of any preceding embodiment, further comprising digitizing electronics configured for storing data on registered fluorescence of particles to allow for analysis of particle characteristics.

15. An apparatus for simultaneous analyzing physical and chemical characteristics of particles in multiple streams of particles, the apparatus comprising: (a) at least one optical excitation source; (b) a first radio-frequency source having a first radio-frequency output; (c) a second radio-frequency source having a second radio-frequency output; (d) an optical, or acousto-optical, combining device including an interferometer with the optical excitation source split into a first arm received at a first acousto-optic device, and a second arm received by a second acousto-optic device, after which the arms of the beam are recombined; (e) wherein said first or second acousto-optic device comprises an acousto-optic deflector (AOD), or an acousto-optic frequency shifter (AOFS); (f) a radio frequency (RF) comb generator configured for driving said acousto-optic deflector (AOD) to generate a set of spatially disparate amplitude modulated beams through beat frequency modulation with sufficient spatial width to span said plurality of focused streams of particles; (g) wherein an optical interrogation beam having a spatially distributed beat frequency is output from said optical, or acousto-optical, combining device; (h) an optical system configured for directing said optical interrogation beam across a plurality of focused streams of particles so that said spatially distributed beat frequency simultaneously spans said plurality of focused streams of particles whose physical and chemical characteristics are being analyzed by said apparatus; and (i) an optical detector configured for registering fluorescence of particles, within said plurality of focused streams of particles, at different modulation frequencies within said spatially distributed beat frequency, wherein fluorescence across multiple focused streams of particles are registered in parallel by said optical detector whose output is configured for receipt by digitizing electronics configured for storing data on registered fluorescence of particles to allow for analysis of particle characteristics.

16. The apparatus of any preceding embodiment, wherein said optical excitation source comprises a laser.

17. The apparatus of any preceding embodiment, wherein said laser comprises a continuous wave laser.

18. The apparatus of any preceding embodiment, wherein said optical combining device, said optical system, or a combination thereof, are configured for independently-controlling illumination directed at each parallel flow stream, toward establishing each flow channel with identical optical sensitivity.

19. The apparatus of any preceding embodiment, wherein said plurality of focused streams of particles are retained in a microfluidic device or chip.

20. The apparatus of any preceding embodiment, further comprising one or more additional optical detectors, which are each configured for registering fluorescence at a different modulation frequency so that different characteristics of particles in each focused stream are detected.

21. The apparatus of any preceding embodiment, further comprising an optical device, or devices, for separating different colors of fluorescence emission so that each of these multiple detectors can analyze fluorescence in a different spectral band associated with different characteristics of particles in each focused stream of particles.

22. The apparatus of any preceding embodiment, wherein each channel of a microfluidic device or chip is exposed to excitation at a different modulation frequency that is unique to that channel by using beat frequency modulation.

23. The apparatus of any preceding embodiment, wherein fluorescence is excited in each channel at a distinct radio-frequency, which allows detection of fluorescence from multiple points using a single photodetector.

24. The apparatus of any preceding embodiment, wherein said particles comprise cells, or portions of cells.

25. The apparatus of any preceding embodiment, further comprising digitizing electronics configured for continuously storing data on registered fluorescence of particles to allow for analysis of particle characteristics.

26. A method for performing flow cytometry in simultaneously interrogating physical and chemical characteristics of particles in multiple streams of particles, the method comprising: (a) introducing fluidic particles, or cells, as targets of interest into a plurality of fluid flow channels; (b) simultaneously exposing the targets to an excitation source as they flow though the fluid flow channels, so that targets in each fluid flow channel are exposed to a different modulated optical beam with a modulation frequency that is unique to that channel; (c) detecting fluorescence from said targets based on excitation at a particular modulation frequency as detected by an optical detector; and (d) outputting fluorescence data of said targets for analysis of physical and chemical characteristics of said targets in a fluid of said fluid flow channels.

27. A method for performing flow cytometry, the method comprising: (a) providing a microfluidic chip having a plurality of parallel flow channels; (b) introducing fluidic targets of interest into a plurality of said parallel flow channels; (c) simultaneously exposing the fluidic targets to an excitation source as they flow though the parallel flow channels; (d) wherein each said parallel flow channel is exposed to a different modulated optical beam with a modulation frequency that is unique to that channel; and (e) using a single detector, detecting fluorescence from the targets based on excitation at a particular modulation frequency to analyze physical and chemical characteristics of particles in a fluid.

28. The method of any preceding embodiment, wherein each channel is exposed to excitation at a different modulation frequency that is unique to that channel by using beat frequency modulation.

29. The method of any preceding embodiment, wherein each wherein each channel is exposed to excitation at a different modulation frequency that is unique to that channel by using a separate modulation source for each channel.

30. The method of any preceding embodiment, wherein fluorescence is excited in each channel at a distinct radiofrequency, which allows detection of fluorescence from multiple points using a single photodetector.

31. The method of any preceding embodiment, wherein excitation occurs at the beat frequency between two interfering, frequency-shifted beams of light.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for simultaneously analyzing physical and chemical characteristics of particles in multiple streams of particles, the apparatus comprising:
   (a) at least one optical excitation source;
   (b) a first radio-frequency source having a first radio-frequency output;
   (c) a second radio-frequency source having a second radio-frequency output;
   (d) an optical, or acousto-optical, combining device configured for combining said first radio-frequency output and said second radio-frequency output into an optical interrogation beam having a spatially distributed beat frequency, wherein said optical interrogation beam comprises a plurality of separate beams configured for being directed to each of a plurality of focused streams;
   (e) an optical system configured for directing said optical interrogation beam across the plurality of focused streams of particles so that said spatially distributed beat frequency simultaneously spans said plurality of focused streams of particles whose physical and chemical characteristics are being analyzed by said apparatus; and
   (f) an optical detector configured for registering fluorescence of particles, within said plurality of focused streams of particles, at different modulation frequencies within said spatially distributed beat frequency, wherein fluorescence across multiple focused streams of particles are registered in parallel by said optical detector.

2. The apparatus as recited in claim 1, wherein said optical excitation source comprises a laser.

3. The apparatus as recited in claim 2, wherein said laser comprises a continuous wave laser.

4. The apparatus as recited in claim 1, wherein said optical combining device, said optical system, or a combination thereof, are configured for independently-controlling illumination directed at each parallel flow stream, toward establishing each flow channel with identical optical sensitivity.

5. The apparatus as recited in claim 1, wherein said plurality of focused streams of particles are retained in a microfluidic device or chip.

6. The apparatus as recited in claim 1, further comprising one or more additional optical detectors, each of which are configured for registering fluorescence at a different modulation frequency so that different characteristics of particles in each focused stream are detected.

7. The apparatus as recited in claim 6, further comprising optical means for separating different colors of fluorescence emission so that each of these multiple detectors can analyze fluorescence in a different spectral band associated with different characteristics of particles in each focused stream of particles.

8. The apparatus as recited in claim 1, wherein each channel of a microfluidic device or chip is exposed to excitation at a different modulation frequency that is unique to that channel by using beat frequency modulation.

9. The apparatus as recited in claim 8, wherein fluorescence is excited in each channel at a distinct radio-frequency, which allows detection of fluorescence from multiple points using a single photodetector.

10. The apparatus as recited in claim 1, wherein said particles comprise cells, or portions of cells.

11. The apparatus as recited in claim 1, wherein said optical, or acousto-optical, combining device comprises an interferometer, with the beam being split with a first arm of the beam received at an first acousto-optic device, and a second arm of the beam received by a second acousto-optic device, after which the arms of the beam are recombined and directed through the optical system.

12. The apparatus as recited in claim 11, wherein said first or second acousto-optic device comprises an acousto-optic deflector (AOD), or an acousto-optic frequency shifter (AOFS).

13. The apparatus as recited in claim 12, further comprising a radio frequency (RF) comb generator configured for driving said acousto-optic deflector thus generating a set of spatially disparate amplitude modulated beams through beat frequency modulation with sufficient spatial width to span said plurality of focused streams of particles.

14. The apparatus as recited in claim 1, further comprising digitizing electronics configured for storing data on registered fluorescence of particles to allow for analysis of particle characteristics.

15. An apparatus for simultaneous analyzing physical and chemical characteristics of particles in multiple streams of particles, the apparatus comprising:
   (a) at least one optical excitation source;
   (b) a first radio-frequency source having a first radio-frequency output;
   (c) a second radio-frequency source having a second radio-frequency output;
   (d) an optical, or acousto-optical, combining device including an interferometer with the optical excitation source split into a first arm received at a first acousto-optic device, and a second arm received by a second acousto-optic device, after which the arms of the beam are recombined;
   (e) wherein said first or second acousto-optic device comprises an acousto-optic deflector (AOD), or an acousto-optic frequency shifter (AOFS);
   (f) a radio frequency (RF) comb generator configured for driving said acousto-optic deflector (AOD) to generate a set of spatially disparate amplitude modulated beams through beat frequency modulation with sufficient spatial width to span said plurality of focused streams of particles;
   (g) wherein an optical interrogation beam having a spatially distributed beat frequency is output from said optical, or acousto-optical, combining device;
   (h) an optical system configured for directing said optical interrogation beam across a plurality of focused streams of particles so that said spatially distributed beat frequency simultaneously spans said plurality of focused streams of particles whose physical and chemical characteristics are being analyzed by said apparatus; and
   (i) an optical detector configured for registering fluorescence of particles, within said plurality of focused streams of particles, at different modulation frequencies within said spatially distributed beat frequency, wherein fluorescence across multiple focused streams of particles are registered in parallel by said optical detector whose output is configured for receipt by digitizing electronics configured for storing data on registered fluorescence of particles to allow for analysis of particle characteristics.

16. The apparatus as recited in claim 15, wherein said optical excitation source comprises a laser.

17. The apparatus as recited in claim 16, wherein said laser comprises a continuous wave laser.

18. The apparatus as recited in claim 15, wherein said optical combining device, said optical system, or a combination thereof, are configured for independently-controlling illumination directed at each parallel flow stream, toward establishing each flow channel with identical optical sensitivity.

19. The apparatus as recited in claim 15, wherein said plurality of focused streams of particles are retained in a microfluidic device or chip.

20. The apparatus as recited in claim 15, further comprising one or more additional optical detectors, which are each configured for registering fluorescence at a different modulation frequency so that different characteristics of particles in each focused stream are detected.

21. The apparatus as recited in claim 20, further comprising an optical device, or devices, for separating different colors of fluorescence emission so that each of these multiple detectors can analyze fluorescence in a different spectral band associated with different characteristics of particles in each focused stream of particles.

22. The apparatus as recited in claim 15, wherein each channel of a microfluidic device or chip is exposed to excitation at a different modulation frequency that is unique to that channel by using beat frequency modulation.

23. The apparatus as recited in claim 22, wherein fluorescence is excited in each channel at a distinct radiofrequency, which allows detection of fluorescence from multiple points using a single photodetector.

24. The apparatus as recited in claim 15, wherein said particles comprise cells, or portions of cells.

25. The apparatus as recited in claim 15, further comprising digitizing electronics configured for continuously storing data on registered fluorescence of particles to allow for analysis of particle characteristics.

26. A method for performing flow cytometry in simultaneously interrogating physical and chemical characteristics of particles in multiple streams of particles, the method comprising:

(a) introducing fluidic particles, or cells, as targets of interest into a plurality of fluid flow channels;

(b) simultaneously exposing the targets to an excitation source as they flow though the fluid flow channels, so that targets in each fluid flow channel are exposed to a different modulated optical beam with a modulation frequency that is unique to that channel;

(c) detecting fluorescence from said targets based on excitation at a particular modulation frequency as detected by an optical detector; and (d) outputting fluorescence data of said targets for analysis of physical and chemical characteristics of said targets in a fluid of said fluid flow channels.

27. A method for performing flow cytometry, the method comprising:

(a) providing a microfluidic chip having a plurality of parallel flow channels;

(b) introducing fluidic targets of interest into a plurality of said parallel flow channels;

(c) simultaneously exposing the fluidic targets to an excitation source as they flow though the parallel flow channels;

(d) wherein each said parallel flow channel is exposed to a different modulated optical beam with a modulation frequency that is unique to that channel; and (e) using a single detector, detecting fluorescence from the targets based on excitation at a particular modulation frequency to analyze physical and chemical characteristics of particles in a fluid.

28. The method as recited in claim 27, wherein each channel is exposed to excitation at a different modulation frequency that is unique to that channel by using beat frequency modulation.

29. The method as recited in claim 27, wherein each wherein each channel is exposed to excitation at a different modulation frequency that is unique to that channel by using a separate modulation source for each channel.

30. The method as recited in claim 27, wherein fluorescence is excited in each channel at a distinct radiofrequency, which allows detection of fluorescence from multiple points using a single photodetector.

31. The method as recited in claim 30, wherein excitation occurs at the beat frequency between two interfering, frequency-shifted beams of light.

* * * * *